United States Patent [19]

Cosgrove et al.

[11] Patent Number: 5,143,714
[45] Date of Patent: Sep. 1, 1992

[54] MATERIAL AND PROCEDURE FOR TESTING AND CONTROL OF IMMUNOSTAINING TECHNIQUES

[75] Inventors: Raymond F. Cosgrove, Wallasey; Terence P. Male, Helsby; Graeme M. Smalley, Manchester, all of England

[73] Assignee: Shandon Scientific Limited, Cheshire, England

[21] Appl. No.: 359,381

[22] Filed: May 31, 1989

[30] Foreign Application Priority Data

Jun. 9, 1988 [GB] United Kingdom ............... 8813628

[51] Int. Cl.⁵ .................. G01N 33/48; G01N 33/563; G01N 33/559; C12Q 1/00
[52] U.S. Cl. ......................................... 424/3; 436/513; 436/515; 436/535; 435/7.1; 435/4; 435/182
[58] Field of Search ............... 436/514, 515, 535, 513; 424/3; 435/7.1, 4, 182

[56] References Cited

U.S. PATENT DOCUMENTS

| | | | |
|---|---|---|---|
| 3,678,151 | 7/1972 | Horonick et al. | 424/3 |
| 3,932,229 | 1/1976 | Grandine | 204/180 |
| 4,198,389 | 4/1980 | Wadsworth | 436/513 |
| 4,305,721 | 12/1981 | Bernstein | 23/230 |
| 4,603,105 | 7/1986 | Kaplan | 435/7 |
| 4,647,543 | 3/1987 | Stöcker | 424/3 |
| 4,695,548 | 9/1987 | Cantor et al. | 435/179 |
| 4,820,504 | 4/1989 | Battifora | 424/3 |
| 4,914,022 | 4/1990 | Furmanski et al. | 435/7 |

FOREIGN PATENT DOCUMENTS

| | | |
|---|---|---|
| 0077477 | 9/1982 | European Pat. Off. . |
| 0266077 | 5/1988 | European Pat. Off. . |

OTHER PUBLICATIONS

Increased Sensitivity in Peroxidase Immunocytochemistry, authored by L. Scopsi and L. I. Larsson (Histochemistry 1986, 84:221).

Microphotometric Quantitation of the Reaction Product of Several Indirect Immunoperoxidase Methods Demonstrating Monoclonal Antibody Binding to Antigens Immobilized on Nitrocellulose, authored by Peter H. Nibbering and Ralph Van Furth, (J. Histochem & Cutochem, 35, 909-916, 1987).

An Artificial Test Substrate for Evaluating Electron Microscopic Immunocytochemical Labeling Reactions, authored by Gerard D. Gagne and Mahlon F. Miller (J. Histochem & Cytochem, 35, 1425-1431, 1987).

Primary Examiner—Glennon H. Hollrah
Assistant Examiner—Gary E. Hollinden
Attorney, Agent, or Firm—Vaden, Eickenroht, Thompson & Boulware

[57] ABSTRACT

A test/control procedure and material is provided to facilitate standardization of immunostaining techniques and the assessment of their results. Pellets of an absorbent gel such as agar gel are caused to adsorb individual specific concentrations of an antigen of interest. The adsorbed antigens are confined to the individual pellets as by fixation or by enclosure in a diffusion-inhibiting barrier, and the pellets are installed in individual wells in a block of the gel in a manner to become integrated therein. The block may then be subjected to the same preparative routines as a tissue sample, sectioned and mounted like the sample, and then subjected to immunostaining by the same routine as the sample sections to provide a valid basis for assessment of the stained sample sections by comparison with the stained gel block sections. A gel block of suitable configuration is also disclosed.

9 Claims, 1 Drawing Sheet

MATERIAL AND PROCEDURE FOR TESTING AND CONTROL OF IMMUNOSTAINING TECHNIQUES

BACKGROUND OF THE INVENTION

1. Field of the Invention

THIS INVENTION relates to immunostaining and especially immunocytochemical (ICC) staining of tissue specimens for diagnostic and related purposes.

2. Background Discussion and the Prior Art

The immunostaining technique, while increasingly widely practiced and subject to the development of automated procedures, is nevertheless difficult to control and critically dependent, for reproducible results, on rigid adherence to operating procedures and conditions and, especially, reagent quality and consistency. Even then the experience of the operator is vital to interpretation of results. Thus the assessment and interpretation of an ICC stain requires considerable experience to discriminate between what is desired specific staining of the chosen antigen and what is artefactual staining of undesirable tissue substrates.

Many parameters are involved in the overall procedure by which a stained specimen is obtained from an original tissue sample and some of those parameters are out of the control of the operator. Those within his control and which may be optimised to preserve and maximally demonstrate the chosen antigen include:
Fixation - type of fixative and duration of fixation Processing - types of reagents and duration of contact with each

---

ICC staining - method; reagent concentrations; incubation times; visualising agent

---

Within each category there are further subdivisions that require control and standardisation. Considering the last category, ICC staining, the operator is not only dependant upon reagent quality but also upon method reproducibility. He therefore assumes that his reagent supplier can guarantee the quality and consistency of reagents so that by eliminating this variable he can direct his efforts to reproducing and standardising his method consistently. This is practicable because variations in the quality of reagents generally only appear in comparisons of the products of different suppliers, accordingly it is quite common for ICC method operators to use reagents from one particular supplier only.

Individuals performing ICC methods, however, do vary in their technique and ability, and whilst method protocols are usually strictly laid down, results are seldom identical between any two operators performing the same method.

A certain degree of control is introduced by using "known positives" and seldom is any interpretation made independently of this control. However, the importance of the preparative, e.g. fixation and processing, steps prior to ICC staining cannot be fully realised, because it has to be assumed that the control or "test" tissue subjected only to the staining routines has previously been prepared by more or less the same protocols as the tissue sample under investigation. Unfortunately this cannot always be the case, especially if material is received from other sources; for instance, typical tissue fixation and processing procedures can account for anything from 30-100% loss of antigenicity from the material. The ICC operator is therefore presented with insurmountable problems when achieving weakly positive or unexpectedly negative results and must try to establish the reason and rectify it by adjusting one of his methods accordingly.

Many of these problems would be overcome if a quantitative "control" could be used at all stages of preparation and staining to evaluate the contribution that each one makes to the overall ICC result.

This control should also take the subjectivity of assessment out of ICC interpretation and indicate the advantages of the use of certain reagents over others in preserving and demonstrating the maximum amount of antigen in tissues.

Accordingly we have been investigating the possibilities for providing a test material that can be subjected to all the preparative procedures to which a tissue sample is subjected and that can therefore be "prepared" alongside a tissue sample to provide a proper basis of comparison with the results of corresponding preparation of the tissue sample.

It was necessary first to demonstrate the practicality of providing on a support, such as to be provided by the sought test material, a range of identifiable standardised specific antigen concentrations capable of being usefully processed by recognised ICC routines to yield consistent and reproducible results, perhaps after extended storage periods prior to processing.

To this end, and based on a study by *Scopsi and Larsson* (Histochemistry 1986, 84:221) into the increased sensitivity in peroxidase immunocytochemistry, an improved, simplified test material model was prepared for such an investigation. Nitrocellulose filters of 0.2 $\mu$m pore size were spotted with 2 $\mu$l droplets of different dilutions of human serum representing different specific antigen concentrations. The serum adsorbed formed spots of 2-3 mm diameter which were then dried, fixed and stained with Sternberger's PAP procedure. Various routines were tested.

It was found that such preparations, once fixed, are stable for many months, yielding reproducible results to a consistent end-point. Other findings include:

1. The existence of optimum dilutions for immune reagents.
2. Reduction in background with a non-ionic detergent such as Triton X in the buffer wash system.
3. Reduction in background with agitation of the buffer wash.
4. Visualisation with DAB chromagen is more sensitive than with AEC.
5. Addition of imidazole to DAB chromagen further improves visualisation.
6. Overnight incubation enables the use of more diluted primary antisera but leads to a slight increase in background.
7. Effect and duration of heat of fixation significantly reduces staining intensity.
8. Slight antigen loss occurs with aqueous formalin fixation.

Unfortunately the model, in this form, cannot be used to look at the effects of tissue processing routines, because nitrocellulose is soluble in alcohols and cannot, therefore, be subjected to such routines.

Paper filters of various grades and makes were similarly assessed in an attempt to overcome the problem of solvency in alcohol. These were found to be unsuitable owing to the following factors:

1. The area of diffusion was too large.
2. Fibres were shed, especially during agitated washing stages, leading to eventual breakdown of the filter paper.
3. Filters became saturated after the addition of two drops of immunoreagent during ICC staining.
4. The final end-point was difficult to determine due to the diffuse area of positivity.
5. All filters demonstrated intense non-specific background staining.

An attempt was made to use cellulose acetate in the same way, but again the spots became diffuse and although this material is resistant to tissue processing alcohols and xylene, considerable fading of the preparations was noticed upon drying out at the end of the procedure.

These findings led us to develop a second model, which used agar as a support medium for the dilutions of serum: as a 1.5% gelled solution, the following advantages are offered:
1. Agar is insoluble in processing reagents
2. It will not melt below 85° C., and is therefore compatible with molten wax (m.p. 60° C.)
3. It allows the diffusion of antibodies and antigens
4. It only stains with acidic dyes
5. It is easy to section
6. It is cheap and widely available.

Moulds of 2.5 cm diameter and 0.5 cm depth were made to receive molten agar. There were 12 circular pegs in each mould so that the agar disc prepared would contain 12 wells. This was to enable small volumes of serum dilutions to be held in defined locations of the disc until diffusion had taken place.

In a series of tests, following diffusion of the serum dilutions into the disc from the well sites, the discs were aqueously fixed and then processed routinely by an overnight schedule using an automatic tissue processing machine such as disclosed in EP-0,077,477.

Sections 5 μm thick obtained by microtomy of the processed discs were stained by the PAP method. Serum as an antigen source processed in this way showed positive staining by ICC, thus proving the feasibility of the technique. Problems became apparent, however, due to the different rates of diffusion shown by the different serum concentrations. As dilutions had been made in Tris-buffered saline (TBS), the higher serum concentrations showed a tendency to diffuse further into the agar. It also became apparent that rates of diffusion were not constant and depended upon the temperature at which the processing occurred.

Another factor influencing the diffusion was found to be time, since even after diffusion appeared to be complete, a dye model showed it to be a continuing process, with the boundaries of the agar disc being the limiting factor. Attempts to overcome these problems were made by:
(i) using solutions of similar viscosity by making the dilutions of human serum in different inert animal sera
(ii) setting a limit to diffusion times prior to fixation.

Animal sera, generally, gave decreased sensitivity after ICC staining. This could be due to the cross-linking of serum antigens and animal serum protein by formaldehyde molecules.

Other minor problems with agar were encountered in sectioning and drying. Preparations appeared to shrink slightly whilst on the water bath. Picking up sections onto glass slides (coated with poly-L-lysine adhesive) and drying was not always successful as occasional floating off of sections was encountered at some stage during the process.

SUMMARY OF THE INVENTION

We have, however, now discovered that the advantages of agar and gels having similar properties as support medium may be realised in practice, and the disadvantages noted above may be overcome, by adsorbing and confining specific antigen concentrations in pellets of gel that are subsequently installed in wells in a gel block.

Thus in accordance with one aspect, the present invention provides a method of preparing a material containing specific antigen concentrations for ICC comparative tests, such method comprising preparing pellets of a suitable gel; subjecting individual pellets to adsorption of specific antigen concentrations; confining the adsorbed antigen concentrations to the respective pellets: and installing the pellets with their respective confined antigen concentrations in individual wells in a block of the gel so as to become integrated therewith.

Preferably the pellets are obtained from the gel block as a consequence of forming wells therein to receive the pellets after the latter have been impregnated and had their respective adsorbed antigen concentrations confined therein.

The necessary attributes of a suitable gel are that it should adsorb required specific antigen concentrations and allow of their processing by ICC routines without interference or unwanted background; and that it should withstand the relevant tissue sample preparative techniques, whether these be regular tissue processing procedures as routinely employed for preparation of embedded tissue samples for sectioning and further processing for ultimate light microscopy examination, or involve cryogenic procedures or the procedures applicable to the preparation of tissue samples for electron microscopy examination. Agar gel has these attributes, preferred gels being those obtained by gelling agar solutions having concentrations within the range 0.5 to 5% by weight. However other gel materials demonstrate these attributes at least to the extent appropriate for certain applications and the following gel materials may be considered: alginic acid; albumin; chrondroitin sulphate.

Diffusion of antigen from pellet to block must be inhibited, and for this reason the adsorbed antigen concentrations must be confined to their respective pellets prior to the installation of the pellets in the block. This can be accomplished by provision of a diffusion-inhibiting barrier, such as a wax coating, on the individual pellets, or by immobilisation of the antigen in each pellet by subjecting the pellets to a fixation procedure such as that used in routine tissue processing.

Depending upon the requirements, the individual pellets to be installed in a test material block may be impregnated with an extended range of concentrations of a simple antigen, or with less extended ranges of concentrations of two or more specific antigens. One or more pellets having zero antigenic material content may be installed in a block to serve as "controls".

Selected pellets and/or the block itself may include added matter intended to produce background staining in use that simulates the background staining of a tissue sample. Such added matter could be proteinaceous material, collagen, sugars and the like.

The invention also provides a test material in the form of a block of gel having installed therein a plurality of gel pellets each impregnated with a specific antigen concentration confined therein.

The gel block of the invention may be treated in the same manner as a tissue sample. That is to say, it may be subjected to processing leading to an embedqed block that may then be sectioned by microtome to provide a thin section capable of being mounted on a microscope slide and which section will incorporate regions corresponding with the embedded pellets in the block. Such a section may then be further processed alongside a tissue sample section and subjected to ICC staining also alongside the tissue specimen to provide a basis for direct comparison between the stained tissue section and the antigen-containing regions of the test block section.

BRIEF DESCRIPTION OF THE DRAWING

The invention is further described in detail with illustration in the accompanying drawing, in which.

DESCRIPTION OF THE EMBODIMENTS

In a typical embodiment of the method of the invention, 2% agar gel is made by dissolving 2 grams of "Lab M Agar 2" in 100 ml of boiling water, the solution then being sterilised by autoclaving. While molten, 2 ml of this solution is poured into a suitable mould to a depth of, say, 5 mm and then left to solidify at room temperature for a duration of approximately 15 minutes. The solidified agar gel is then extracted from the mould and placed at 37° C. for 15 minutes in an incubator for the purpose of removing residual surface moisture.

A desirable shape for the mould is a rectangle with a notched corner for identification purposes. However, the mould may be of another shape and the solidified agar gel be subsequently cut to a desired - e.g. rectangular - shape. A preferred final shape, direct from the mould or produced by cutting from a larger plate, is illustrated at 10 in FIG. 1 and is a square, 20×20 mm with a notched corner 11.

Figure 1:
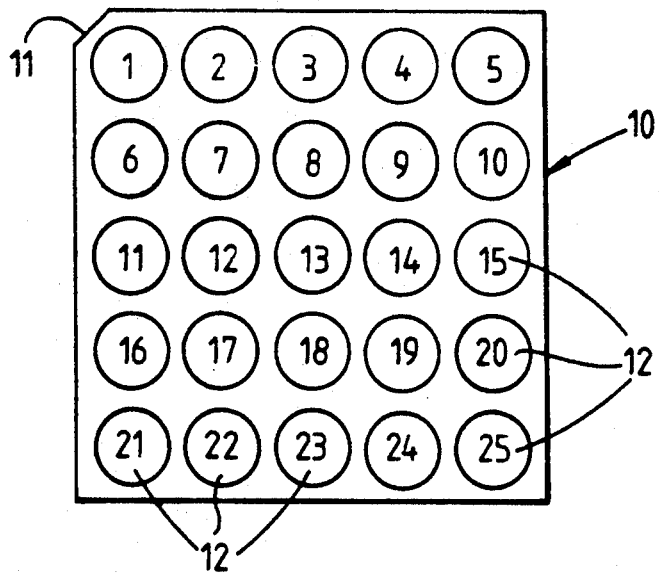
FIG. 1 is a plan representation of a gel block formed with twenty five wells to receive gel pellets with antigen concentrations confined therein, for practice of the method of the invention.

The moulded or cut to shape plate thus obtained is placed upon a moist filter paper and cylindrical pellets are removed from this plate, using, for instance, a well cutter of 1.5 or 2.5 mm diameter. The pellets are desirably removed at points on a rectangular grid notionally superimposed on the plate. A 5×5 grid is convenient when the pellets are formed by using a 1.5 mm well cutter. FIG. 1 shows the plate 10 with twenty five wells 12 formed therein by removing pellets 13 (FIG. 2) therefrom in this way. The wells are numbered 1 to 25 in the drawing for identification purposes.

Figure 2:
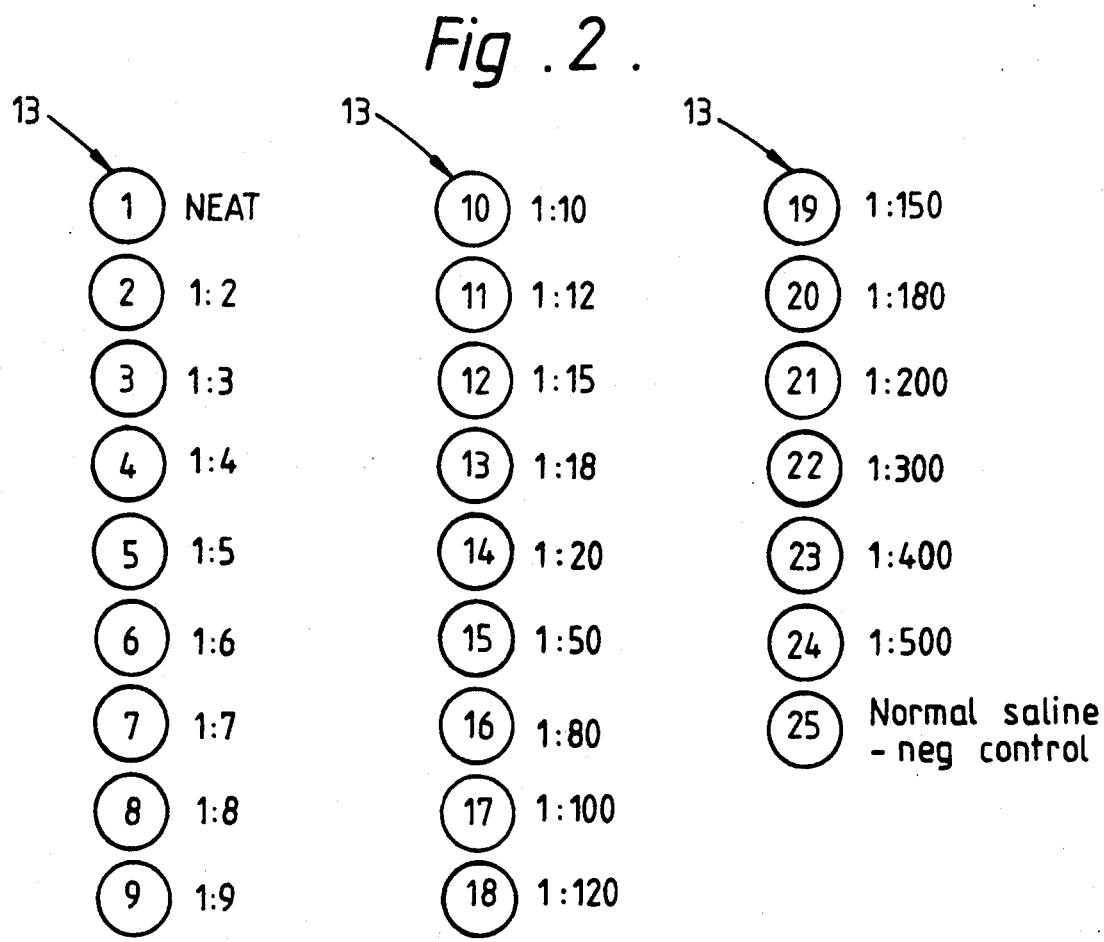
FIG. 2 is a corresponding plan representation of twenty five gel pellets for installation in the wells of the gel block of FIG. 1, with a typical scheme of impregnation of the individual pellets in the practice of the invention.

Each pellet is then placed in a separate microcentrifuge tube or like container holding a specific antigen concentration. In the case of a specific antigen, the concentrations may cover the dilution range 1:0 to 1:500 and at least one pellet may be used as a negative control by being impregnated with non-anti-genic material, for example normal saline. The pellets are allowed to adsorb and become impregnated with the respective antigen concentrations (and control material) for a period of 60 minutes, at the end of which the pellets are fixed by immersion in 10% formalin at room temperature, to immobilise the antigen and to inhibit its subsequent diffusion out of the pellets. The fixed pellets are then installed in the wells from which they were removed in the original agar gel plate. The pellets may be arranged in the gel block in any appropriate order related to their antigenic content, and conveniently so that visual cut-off demonstrating acceptability of staining is evident. FIG. 2 shows twenty five pellets 12, numbered 1 to 25 in correspondence with the numbering of the wells in FIG. 1 to show the favoured locations of the respective pellets 13 in the wells 12 of the plate 10 of FIG. 1, when the pellets have been impregnated with antigen concentrations (or control material - normal saline in the case of pellet No. 25) corresponding with the dilution ratios shown alongside the individual pellets in FIG. 2.

The agar gel plate with the installed impregnated and fixed pellets is capable of long term storage under suitable conditions. A moisture-retentive packaging will usually be required and if the plate is unfixed it will need storage at 4° C. or lower. Preservatives such as sodium azide may be incorporated.

The agar plate with installed impregnated pellets may be subjected to processing in the same manner as a tissue sample. For instance it may be subjected to automated processing alongside tissue samples in a tissue processor such as disclosed in EP-0,077,477, using a routine processing schedule that results in the processed plate being embedded in, e.g., wax. This embedded plate may be coarsely trimmed and then sliced by a microtome into, e.g. 5 μm sections in the same manner as a processed tissue sample. The sections may be mounted on glass slides coated with 0.1 percent poly-L-lysine, and dried at 37° C. for, say, sixty minutes in an incubator.

Slide mounted sections are also capable of long term storage under appropriate conditions such as employed for storage of mounted tissue sample sections.

The slide mounted sections may be subjected to typical ICC procedures. Preferably the slide mounted sections would be pre-heated to 60° C. for fifteen minutes in a hot air oven to condition them for the further processing and also to ensure their attachment to the glass slides.

In a typical ICC procedure a slide mounted section would first be de-waxed and rehydrated by immersion in xylene and then sequentially in successive alcohol solutions of diminishing concentration to a final immersion in water. Thereafter the section would be washed in Tris-buffered saline (TBS) for five minutes with agitation. The area around the mounted section would then be dried and two to three drops of primary antibody such as IgG 1:800 applied and incubated for thirty minutes. The section would then be rinsed and washed for five minutes with agitation in TBS, then dried around again prior to the addition of two to three drops of secondary antibody such as swine anti-rabbit diluted 1:100. After twenty minutes further incubation the section would again be rinsed and washed in TBS for five minutes and then dried around. Two to three drops of peroxidase, PAP rabbit diluted 1:100, would then be applied for twenty minutes incubation. Thereafter the section would be washed finally in TBS and developed by staining with DAB chromogen solution for two minutes. The developed section would then be rinsed, washed in TBS, dehydrated, cleared and mounted.

The developed and mounted section displays spots of differing stain density that are directly related to the original specific antigen concentrations with which the pellets were impregnated in the production of the test block. Accordingly, the stain density of a correspondingly treated tissue specimen may be compared qualitatively and/or quantitatively with the test section spots for evaluation of the antigenicity of the tissue sample.

We claim:

1. A test material comprising a gel block having installed at discrete separated locations therein a plurality of gel pellets formed from the same gel material from which said gel block is formed individually impregnated with specific antigen concentration confined to the respective pellets.

2. The test material of claim 1, in which said block and said pellets are formed of gelled agar solution.

3. The test material of claim 1 or 2, in which said block is rectangular in plan and said pellets are installed therein in a lattice array.

4. The test material of claim 3, wherein said block has a thickness of about 5 mm.

5. The test material of claim 4, in which said block is in the form of a square plate about 20 mm × 20 mm with an identifiable corner.

6. The test material of claim 1, at least partly processed and embedded by a tissue processing routine.

7. The test material of claim 6, comprising mounted thin sections of the embedded processed block, each section including a section of each of the said pellets.

8. The test material of claim 7, comprising a said mounted section that has been subjected to ICC staining routines.

9. A test material comprising a gel block having installed therein a plurality of gel pellets individually impregnated with specific antigen concentrations confined to the respective pellets, and prepared by a method including the steps of subjecting individual pellets to adsorption of specific antigen concentrations, confining the adsorbed antigen concentrations are to the respective gel pellets, and installing the pellets with their respective confined antigen concentrations in individual wells in a block of the gel so as to become integrated therewith.

* * * * *